United States Patent
Rosen et al.

(10) Patent No.: US 11,974,816 B2
(45) Date of Patent: May 7, 2024

(54) AUTOMATED CONTROL AND POSITIONING SYSTEMS FOR DERMATOLOGICAL CRYOSPRAY DEVICES

(71) Applicant: R2 Technologies, Inc., San Ramon, CA (US)

(72) Inventors: Jesse Rosen, Albany, CA (US); Erica Elford, San Mateo, CA (US); Dylan McReynolds, Berkeley, CA (US); Erik Stauber, Albany, CA (US)

(73) Assignee: R2 Technologies, Inc., San Ramon, CA (US)

( * ) Notice: Subject to any disclaimer, the term of this patent is extended or adjusted under 35 U.S.C. 154(b) by 963 days.

(21) Appl. No.: 16/723,633

(22) Filed: Dec. 20, 2019

(65) Prior Publication Data

US 2020/0197104 A1    Jun. 25, 2020

Related U.S. Application Data

(60) Provisional application No. 62/784,052, filed on Dec. 21, 2018.

(51) Int. Cl.
*A61B 34/20* (2016.01)
*A61B 18/00* (2006.01)
(Continued)

(52) U.S. Cl.
CPC .......... *A61B 34/20* (2016.02); *A61B 18/0218* (2013.01); *A61B 18/201* (2013.01);
(Continued)

(58) Field of Classification Search
CPC ........... A61B 2018/00053; A61B 2018/00452; A61B 2018/00696; A61B 2018/00773;
(Continued)

(56) References Cited

U.S. PATENT DOCUMENTS

| 3,664,344 A | 5/1972 | Bryne |
| 4,206,609 A | 6/1980 | Durenec et al. |

(Continued)

FOREIGN PATENT DOCUMENTS

| CN | 104394813 A | 3/2015 |
| EP | 1797847 | 6/2007 |

(Continued)

OTHER PUBLICATIONS

Andrews, Cryosurgery for Common Skin Conditions, American Family Physician, vol. 69, Issue 10, May 15, 2004, pp. 2365-2372.
(Continued)

*Primary Examiner* — Kaitlyn E Smith
*Assistant Examiner* — Bradford C. Blaise
(74) *Attorney, Agent, or Firm* — Kilpatrick Townsend & Stockton LLP

(57) ABSTRACT

The present is directed to improved systems and methods for skin cooling treatments. A skin cooling treatment system can include a mechanical arm that can have a proximal end and an distal end. The system can include a processor that can control the mechanical arm, and a cryospray applicator. The cryospray applicator can be coupled to the distal end of the mechanical arm and can be moveable by the mechanical arm to deliver a spray of cryogen to a portion of an area of skin tissue for treatment. The cryospray applicator can include an array of orifices through which the cryogen can be sprayed.

25 Claims, 7 Drawing Sheets

(51) Int. Cl.
*A61B 18/02* (2006.01)
*A61B 18/20* (2006.01)

(52) U.S. Cl.
CPC .............. *A61B 2018/00053* (2013.01); *A61B 2018/00452* (2013.01); *A61B 2018/00696* (2013.01); *A61B 2018/00773* (2013.01); *A61B 2018/0231* (2013.01); *A61B 2562/04* (2013.01)

(58) Field of Classification Search
CPC ................ A61B 18/02; A61B 18/0218; A61B 2018/0231; A61B 34/10; A61B 34/20; A61B 34/30; A61B 2034/107
See application file for complete search history.

(56) References Cited

U.S. PATENT DOCUMENTS

| | | | |
|---|---|---|---|
| 4,946,460 | A | 8/1990 | Merry et al. |
| 5,531,742 | A | 7/1996 | Barken |
| 5,596,875 | A | 1/1997 | Berry et al. |
| 5,759,182 | A | 6/1998 | Varney et al. |
| 5,848,981 | A | 12/1998 | Herbranson |
| 5,901,707 | A | 5/1999 | Goncalves |
| 6,017,337 | A | 1/2000 | Pira |
| 6,139,544 | A | 10/2000 | Mikus et al. |
| 6,226,996 | B1 | 5/2001 | Weber et al. |
| 6,235,018 | B1 | 5/2001 | LePivert |
| 6,413,252 | B1 | 7/2002 | Zavislan |
| 6,430,956 | B1 | 8/2002 | Haas et al. |
| 6,503,246 | B1 | 1/2003 | Har-shai et al. |
| 6,629,417 | B2 | 10/2003 | Haas et al. |
| 6,669,688 | B2 | 12/2003 | Svaasand et al. |
| 6,960,202 | B2 | 11/2005 | Cluzeau et al. |
| 6,981,970 | B2 | 1/2006 | Karni |
| 7,367,341 | B2 | 5/2008 | Anderson et al. |
| 7,422,576 | B2 | 9/2008 | Boynton et al. |
| 7,630,774 | B2 | 12/2009 | Karni et al. |
| 7,751,452 | B2 | 7/2010 | Vogler |
| 7,780,656 | B2 | 8/2010 | Tankovich |
| 7,824,395 | B2 | 11/2010 | Chan et al. |
| 7,850,683 | B2 | 12/2010 | Elkins et al. |
| 7,962,192 | B2 | 6/2011 | Bodduluri et al. |
| 7,963,959 | B2 | 6/2011 | Da Silva et al. |
| 8,150,532 | B2 | 4/2012 | Karni et al. |
| 8,308,717 | B2 | 11/2012 | Rapoport |
| 8,435,194 | B2 | 5/2013 | Dverin et al. |
| 8,562,597 | B2 | 10/2013 | Van Der Heijden et al. |
| 8,579,835 | B2 | 11/2013 | Britva et al. |
| 8,764,701 | B1 | 7/2014 | Hicks |
| 8,769,733 | B2 | 7/2014 | Galyean et al. |
| 8,950,406 | B2 | 2/2015 | Karni et al. |
| 9,050,117 | B2 | 6/2015 | Nelson et al. |
| 9,241,753 | B2 | 1/2016 | Fourkas et al. |
| 9,326,808 | B2 | 5/2016 | Damasco et al. |
| 9,522,031 | B2 | 12/2016 | Anderson et al. |
| 9,545,284 | B2 | 1/2017 | Karni |
| 9,549,773 | B2 | 1/2017 | Anderson et al. |
| 9,597,528 | B2 | 3/2017 | Schomacker et al. |
| 9,675,419 | B2 | 6/2017 | Akeel et al. |
| 9,724,150 | B1 | 8/2017 | Bao et al. |
| 9,974,684 | B2 | 5/2018 | Anderson et al. |
| 10,118,051 | B2 | 11/2018 | Taghizadeh |
| 10,299,871 | B2 | 5/2019 | Zingaretti et al. |
| 10,349,997 | B1 | 7/2019 | O'Reilly |
| 2003/0100936 | A1 | 5/2003 | Altshuler et al. |
| 2004/0167592 | A1 | 8/2004 | Grove et al. |
| 2005/0222565 | A1 | 10/2005 | Manstein |
| 2006/0058238 | A1 | 3/2006 | Laurent-Applegate et al. |
| 2006/0155267 | A1 | 7/2006 | Berzak et al. |
| 2006/0189976 | A1 | 8/2006 | Karni et al. |
| 2006/0206103 | A1 | 9/2006 | Altshuler et al. |
| 2006/0282067 | A1 | 12/2006 | Koop et al. |
| 2007/0088386 | A1 | 4/2007 | Babaev |
| 2007/0129714 | A1 | 6/2007 | Elkins et al. |
| 2007/0135876 | A1 | 6/2007 | Weber |
| 2007/0185527 | A1 | 8/2007 | Babaev |
| 2008/0039747 | A1 | 2/2008 | Baerwalde et al. |
| 2008/0071332 | A1 | 3/2008 | Nelson et al. |
| 2008/0119828 | A1 | 5/2008 | Nelson et al. |
| 2008/0119839 | A1 | 5/2008 | Vancelette |
| 2008/0183164 | A1 | 7/2008 | Elkins et al. |
| 2008/0183167 | A1 | 7/2008 | Britva et al. |
| 2008/0287943 | A1 | 11/2008 | Weber et al. |
| 2009/0012585 | A1 | 1/2009 | Karni et al. |
| 2009/0171424 | A1 | 7/2009 | Britva et al. |
| 2009/0281537 | A1 | 11/2009 | Britva et al. |
| 2010/0036295 | A1 | 2/2010 | Altshuler et al. |
| 2010/0087806 | A1 | 4/2010 | Da Silva et al. |
| 2010/0114007 | A1 | 5/2010 | Fischer et al. |
| 2011/0162390 | A1 | 7/2011 | Littrup et al. |
| 2011/0313411 | A1 | 12/2011 | Anderson et al. |
| 2012/0041525 | A1 | 2/2012 | Karni |
| 2012/0071794 | A1 | 3/2012 | Karni |
| 2012/0123319 | A1 | 5/2012 | Britva et al. |
| 2012/0330194 | A1 | 12/2012 | Britva et al. |
| 2013/0296812 | A1 | 11/2013 | Bangera et al. |
| 2014/0007895 | A1 | 1/2014 | Britva et al. |
| 2014/0135662 | A1 | 5/2014 | Britva et al. |
| 2014/0303696 | A1 | 10/2014 | Anderson et al. |
| 2014/0303697 | A1 | 10/2014 | Anderson et al. |
| 2015/0045857 | A1 | 2/2015 | Britva et al. |
| 2015/0080991 | A1 | 3/2015 | Britva et al. |
| 2015/0216720 | A1 | 8/2015 | DeBenedictis et al. |
| 2015/0223975 | A1 | 8/2015 | Anderson et al. |
| 2016/0051401 | A1 | 2/2016 | Yee et al. |
| 2016/0135985 | A1 | 5/2016 | Anderson et al. |
| 2016/0157915 | A1 | 6/2016 | Anderson et al. |
| 2016/0287867 | A1 | 10/2016 | Rubinsky et al. |
| 2017/0020636 | A1 | 1/2017 | Akeel et al. |
| 2017/0065323 | A1 | 3/2017 | Rosen et al. |
| 2017/0231721 | A1 | 8/2017 | Akeel et al. |
| 2017/0348143 | A1 | 12/2017 | Rosen et al. |
| 2018/0028253 | A1 | 2/2018 | Anderson et al. |
| 2018/0360520 | A1 | 12/2018 | Avalle |
| 2019/0047145 | A1 | 2/2019 | Akeel et al. |
| 2019/0239938 | A1 | 8/2019 | Kazic et al. |

FOREIGN PATENT DOCUMENTS

| | | |
|---|---|---|
| EP | 2201917 | 6/2010 |
| EP | 2272455 | 1/2011 |
| GB | 2286660 | 8/1995 |
| JP | H04133822 A | 5/1992 |
| JP | 10052475 | 2/1998 |
| JP | 2005237908 | 9/2005 |
| KR | 200431404 | 11/2006 |
| KR | 100802155 | 2/2008 |
| RU | 2074680 | 3/1997 |
| WO | 2003/078596 A2 | 9/2003 |
| WO | 2003/078596 A3 | 9/2003 |
| WO | 2005/096979 | 10/2005 |
| WO | 2006/066226 | 6/2006 |
| WO | 2006/127467 | 11/2006 |
| WO | 2007/064718 | 6/2007 |
| WO | 2008/055243 | 5/2008 |
| WO | 2008/083305 | 7/2008 |
| WO | 2008/091983 | 7/2008 |
| WO | 2009/146053 | 12/2009 |
| WO | 2010/017477 | 2/2010 |
| WO | 2013/075006 | 5/2013 |
| WO | 2013/075016 | 5/2013 |
| WO | 2016/022347 A1 | 2/2016 |
| WO | 2017/041022 | 3/2017 |
| WO | 2017223120 A1 | 6/2017 |
| WO | 2017/181156 A1 | 10/2017 |
| WO | 2017210619 A1 | 12/2017 |
| WO | 2018/093964 A1 | 5/2018 |
| WO | 2019/089995 A1 | 5/2019 |

OTHER PUBLICATIONS

Gage et al., Critical Temperature for Skin Necrosis in Experimental Cryosurgery, Cryobiology, vol. 19, 1982, pp. 273-282.

(56) References Cited

OTHER PUBLICATIONS

Gage et al., Sensitivity of Pigmented Mucosa and Skin to Freezing Injury, Cryobilogy, vol. 16, 1979, pp. 348-361.
Har-Shai et al., Effect of Skin Surface Temperature on Skin Pigmentation During Contact and Intralesional Cryosurgery of Hypertrophic Scars and Kleoids, Journal of the European Academy of Dermatology and Venereology, vol. 21, No. 2, Feb. 2007, pp. 191-198.
Thai et al., Cryosurgery of Benign Skin Lesions, Australasian Journal of Dermatology, vol. 40, 1999, pp. 175-186.
Yeh, Cryosurgical Treatment of Melanin-Pigmented Gingiva, Oral Surgery, Oral Medicine, Oral Pathology, Oral Radiology, and Endodontology, vol. 86, Issue 6, Jun. 1998, pp. 660-663.
Zachariassen et al., Ice Nucleation and Antinucleation in Nature, Cryobiology, vol. 41, Issue 4, Dec. 2000, pp. 257-279.

AUTOMATED CONTROL AND POSITIONING SYSTEMS FOR DERMATOLOGICAL CRYOSPRAY DEVICES

CROSS-REFERENCES TO RELATED APPLICATIONS

The present application claims the benefit of priority of U.S. Provisional Application No. 62/784,052 filed on Dec. 21, 2018; the entirety of which is hereby incorporated by reference herein.

BACKGROUND OF THE INVENTION

Cryotherapy is the local or general use of cold in medical therapy. Cryotherapy can include the controlled freezing of biological tissue, which controlled freezing of biological tissue, such as skin tissue, can produce various effects. Certain tissue freezing procedures and devices, such as conventional cryoprobes, can cause severe freezing of tissue and generate cellular and visible skin damage.

There is a demand for cosmetic products that can lighten the appearance of skin or otherwise controllably affect skin pigmentation. For example, it may be desirable to lighten the overall complexion or color of a region of skin to alter the general appearance for cosmetic reasons. Also, lightening of particular hyperpigmented regions of skin, such as freckles, 'café au lait' spots, melasma, solar lentigines, or dark circles under the eyes that may result from excessive local amounts of pigment in the skin, may also be desirable for cosmetic reasons. Hyperpigmentation can result from a variety of factors such as UV exposure, aging, stress, trauma, inflammation, etc. Such factors can lead to an excess production of melanin, or melanogenesis, in the skin by melanocytes, which can lead to formation of hyperpigmented areas. Such hyperpigmented areas are typically associated with excess melanin within the epidermis and/or dermal-epidermis junction. However, hyperpigmentation can also result from excess melanin deposited within the dermis.

Hypopigmentation of skin tissue has been observed as a side effect in response to temporary cooling or freezing of the tissue, such as may occur during conventional cryosurgery procedures. Loss of pigmentation following skin cooling or freezing may result from decreased melanin production, decreased melanosome production, destruction of melanocytes, or inhibited transfer or regulation of melanosomes into the keratinocytes in the lower region of the epidermal layer. The resultant hypopigmentation may be long-lasting or permanent. However, it has also been observed that some of these freezing procedures can generate regions of hyperpigmentation (or skin darkening) of skin tissue. The level of increase or decrease in pigmentation may be dependent upon certain aspects of the cooling or freezing conditions, including the temperature of the cooling treatment, and the length of time the tissue is maintained in a frozen state.

Improved hypopigmentation treatments, devices, and systems have been developed to improve the consistency of skin freezing and the overall hypopigmentation consistency. For example, it has been observed that moderate degrees of freezing (e.g., −4 to −30 degrees Celsius) at shorter time frames (e.g., 30 to 60 seconds) can produce particular dermatological effects, such as affecting the expression of skin pigmentation (e.g., hypopigmentation). Cryotherapy can be provided using a variety of techniques including the direct application of a cryogen spray to the skin of the patient or the application of a cooled probe or plate to the skin of the patient. Exemplary methods and devices are described in: U.S. Patent Publication No. 2011/0313411, filed on Aug. 7, 2009, and entitled "METHOD AND APPARATUS FOR DERMATOLOGICAL HYPOPIGMENTATION"; U.S. Patent Publication No. 2014/0303696, filed on Nov. 16, 2012, and entitled "METHOD AND APPARATUS FOR CRYOGENIC TREATMENT OF SKIN TISSUE"; U.S. Patent Publication No. 2014/0303697, filed on Nov. 16, 2012, and entitled "METHOD AND APPARATUS FOR CRYOGENIC TREATMENT OF SKIN TISSUE"; U.S. Patent Publication No. 2015/0223975, filed on Feb. 12, 2015, and entitled "METHOD AND APPARATUS FOR AFFECTING PIGMENTATION OF TISSUE"; U.S. Patent Publication No. 2017/0065323, filed on Sep. 6, 2016, and entitled "MEDICAL SYSTEMS, METHODS, AND DEVICES FOR HYPOPIGMENTATION COOLING TREATMENTS", the entirety of each of which is hereby incorporated by reference herein.

While the treatment of skin or a localized lesion to affect pigmentation can be accomplished with cryotherapy, it may be desirable to provide improved methods, systems, and devices for cryotherapy. In particular, improved designs, controls and parameters associated with cryogen delivery to achieve consistent and reliable skin freezing and desired skin treatment effect may be of benefit. Accordingly, improved dermatological cryospray methods, systems, and devices are desirable.

BRIEF SUMMARY OF THE INVENTION

The present invention relates to improved systems, devices, and methods of delivery of a cryogen to the skin of a patient for skin treatment. More specifically, the present invention relates to improved dermatological cryospray methods, devices, and systems that provide consistency of skin treatment by reliably freezing the skin during treatment while limiting adverse side effects from the skin freezing. Exemplary embodiments include a mechanical arm having a proximal end and a distal end, and a cryospray applicator coupled to the distal end of the mechanical arm. The mechanical arm can be a robotic mechanical arm and/or a teleoperated mechanical arm. The mechanical arm can have a desired number of axes of movement, and can be, for example, a six axis mechanical arm. The mechanical arm can include a plurality of linkages coupled by joints, which joints allow relative movement of the linkages. The mechanical arm can include actuators that can, in response to control signals, affect relative position of some or all of the linkages of the mechanical via movements of some or all of the joints coupling linkages to thereby change a position and/or orientation of the cryospray applicator. The control signals that control the actuators of the mechanical arm can be generated by a processor that can be communicatively coupled with the actuators of the mechanical arm. The processor can generate control signals to control the orientation of the cryospray applicator, the distance separating the cryospray applicator from the patient's skin tissue that is being treated, and/or the cooling being applied to the patient's skin tissue that is being treated.

The cryospray applicator can include an array of orifices through which a cryogen can be dispensed to cool a patient's tissue to provide treatment to the patient's tissue. The cryospray applicator can further include a plurality of sensors that can, in some embodiments, be arranged around the array of orifices. These sensors can sense distance separating the array of orifices from the skin tissue being treated and/or the orientation of the cryospray applicator with respect to the skin tissue. These sensors can maintain a constant distance separating the cryospray applicator from the patient's skin and can maintain the array of orifices in an orientation such that the cryogen sprayed from the array of orifices is sprayed perpendicular to the treated skin tissue of the patient.

One aspect of the present disclosure relates to a method of cooling an area of skin tissue of a patient. The method can include automatically positioning a cryospray applicator proximate to the area of skin tissue of the patient to be treated via movement of a mechanical arm coupled to the cryospray applicator. The method can include directing a spray of cryogen through an array of orifices of the cryospray applicator to cool a portion of the area of skin tissue of the patient. The method can include advancing the cryospray applicator via movement of the mechanical arm to change the portion of the area of skin tissue of the patient cooled by the spray of cryogen. The method can include automatically adjusting positioning of the cryospray applicator with respect to the portion of the area of skin tissue of the patient while the cryospray applicator is advancing.

In some embodiments, automatically adjusting positioning of the cryospray applicator with respect to the portion of the area of skin tissue of the patient can include adjusting at least one of: a distance between the cryospray applicator and the portion of the area of skin tissue of the patient; and an orientation of the cryospray applicator with respect to the portion of the area of skin tissue of the patient. In some embodiments, automatically adjusting a distance between the cryospray applicator and the portion of the area of skin tissue can include: detecting a distance between the cryospray applicator and the portion of the area of skin tissue with at least one distance sensor coupled to the cryospray applicator. In some embodiments, automatically adjusting an orientation of the cryospray applicator with respect to the portion of the area of skin tissue of the patient can include: detecting an orientation of the cryospray applicator with respect to the portion of the area of skin tissue with at least one alignment sensor.

In some embodiments, directing the spray of cryogen through the array of orifices of the cryospray applicator to cool the portion of the area of skin tissue of the patient deforms the portion of the area of skin tissue of the patient. In some embodiments, the orientation of the cryospray applicator is adjusted based at least in part on the deformation of the portion of the area of skin tissue of the patient. In some embodiments, the distance between the cryospray applicator and the portion of the area of the skin tissue of the patient is adjusted based at least in part on the deformation of the portion of the area of skin tissue of the patient. In some embodiments, the method includes detecting a temperature of the portion of the area of skin tissue, and modifying at least one of: advancing the cryospray applicator; a distance between the cryospray applicator and the portion of the area of skin tissue of the patient; or a cryogen delivery rate.

In some embodiments, an infrared camera detects the temperature of the portion of the area of skin tissue. In some embodiments, detecting the temperature of the portion of the area of skin tissue can include: detecting freezing of the portion of the area of skin tissue; or detecting a cooling rate of the portion of the area of skin tissue. In some embodiments, modifying the distance between the cryospray applicator and the portion of the area of skin tissue of the patient can include: changing a distance between the cryospray applicator and the portion of the area of skin tissue of the patient, which portion can include tissue treated by the spray of cryogen; determining an updated portion based on the changed distance; and generating an updated treatment path.

In some embodiments, the method can include advancing the cryospray applicator according to the updated treatment path.

In some embodiments, modifying the cryogen delivery rate can include decreasing a number of open orifices in the cryospray applicator. In some embodiments, modifying the cryogen delivery rate can include decreasing a cryogen pressure at the orifices in the cryospray applicator.

In some embodiments, the mechanical arm can be a 6-axis mechanical arm. In some embodiments, the mechanical arm can be a robotic arm. In some embodiments, the mechanical arm can be a teleoperated arm. In some embodiments, positioning the cryospray applicator proximate to area of the skin tissue of the patient can include moving the cryospray applicator over the portion of the area of the skin tissue of the patient; determining an initial distance separating the cryospray applicator and the portion of the skin tissue; and adjusting the initial distance.

One aspect of the present disclosure relates to a skin cooling treatment system. The system includes a mechanical arm having a proximal end and a distal end and a processor configured to control the mechanical arm. The system can include a cryospray applicator coupled to the distal end of the mechanical arm. The cryospray applicator can include an array of orifices. In some embodiments, the cryospray applicator is moveable by the mechanical arm to deliver a spray of cryogen to a portion of an area of skin tissue for treatment.

In some embodiments, the mechanical arm can be a 6-axis mechanical arm. In some embodiments, the mechanical arm can be a robotic arm. In some embodiments, the cryospray applicator can include at least one distance sensor that can to detect the distance between the cryospray applicator and the portion of the area of skin tissue for treatment at which the spray of cryogen is directed. In some embodiments, the at least one distance sensor can include two distance sensors arranged around the array of orifices. In some embodiments, the two distance sensors include: a first distance sensor at a first position offset from the array of orifices, the first distance sensor having a first orientation; and a second distance sensor at a second position offset from array of orifices, the second distance sensor having a second orientation. In some embodiments, each of the first orientation and the second orientation are directed towards a line of spray of the cryospray applicator.

In some embodiments, the cryospray applicator can include at least one alignment sensor that can detect an orientation of the cryospray applicator with respect to the portion of the area of skin tissue. In some embodiments, the at least one alignment sensor can include three alignment sensors each facing in a common direction, the three alignment sensors radially arranged around the array of orifices of the cryospray applicator.

In some embodiments, the processor can control movement of the distal end of the mechanical arm. In some embodiments, the processor can control movement of the cryospray applicator and a distance between the cryospray applicator and the portion of the area of skin tissue. In some embodiments, the processor can control the distance between the cryospray applicator and the portion of the area of skin tissue based on outputs of the at least one distance sensor.

In some embodiments, the processor can control the orientation of the cryospray applicator with respect to the portion of the area of skin tissue. In some embodiments, the processor can control the orientation of the cryospray applicator with respect to the portion of the area of skin tissue based on outputs of the at least one alignment sensor. In some embodiments, the cryospray applicator further includes temperature detection feature configured to detect a temperature of the portion of the area of skin tissue of the patient. In some embodiments, the temperature detection feature can be an infrared camera. In some embodiments, the temperature detection feature can detect freezing of the portion of the area of skin tissue or detect a freezing rate of the portion of the area of skin tissue.

In some embodiments, the processor can control advancing the cryospray applicator via movement of the mechanical arm to change the portion of the area of skin tissue of the patient cooled by the spray of cryogen, detect a temperature of the portion of the area of skin tissue and modify at least one of: the advancing the cryospray applicator, a distance between the cryospray applicator and the portion of the area of skin tissue of the patient, or a cryogen delivery rate. In some embodiments, modifying the distance between the cryospray applicator and the portion of the area of skin tissue of the patient can include changing a distance between the cryospray applicator and the portion of the area of skin tissue of the patient, which portion includes tissue treated by the spray of cryogen; determining an updated portion based on the changed distance; and generating an updated treatment path. In some embodiments, the processor is configured to control advancing of the cryospray applicator according to the updated treatment path. In some embodiments, modifying the cryogen delivery rate can include decreasing a number of open orifices in the cryospray applicator. In some embodiments, modifying the cryogen delivery rate can include decreasing a cryogen pressure at the orifices in the cryospray applicator.

DETAILED DESCRIPTION OF THE INVENTION

Cooling based treatments are frequently used to address a wide range of health and aesthetic issues. Some of these treatments have been specifically designed to create skin lightening. This skin lightening may be localized to a small skin area, or may affect a large area of skin The area of the to be treated skin can make such treatment difficult as adequate consistency of treatment may be difficult to achieve. These treatments can include cooling treated skin to specific temperatures and/or temperature ranges, and in some instances can include maintaining those temperatures and/or temperature ranges for a predetermined time and/or range of times. In some instances, the effectiveness of many treatments is dependent on the providing of specific amounts of cooling for specific amounts of time. Further, the difficulty in achieving consistent results increases as the treated area increases.

Figure 1:
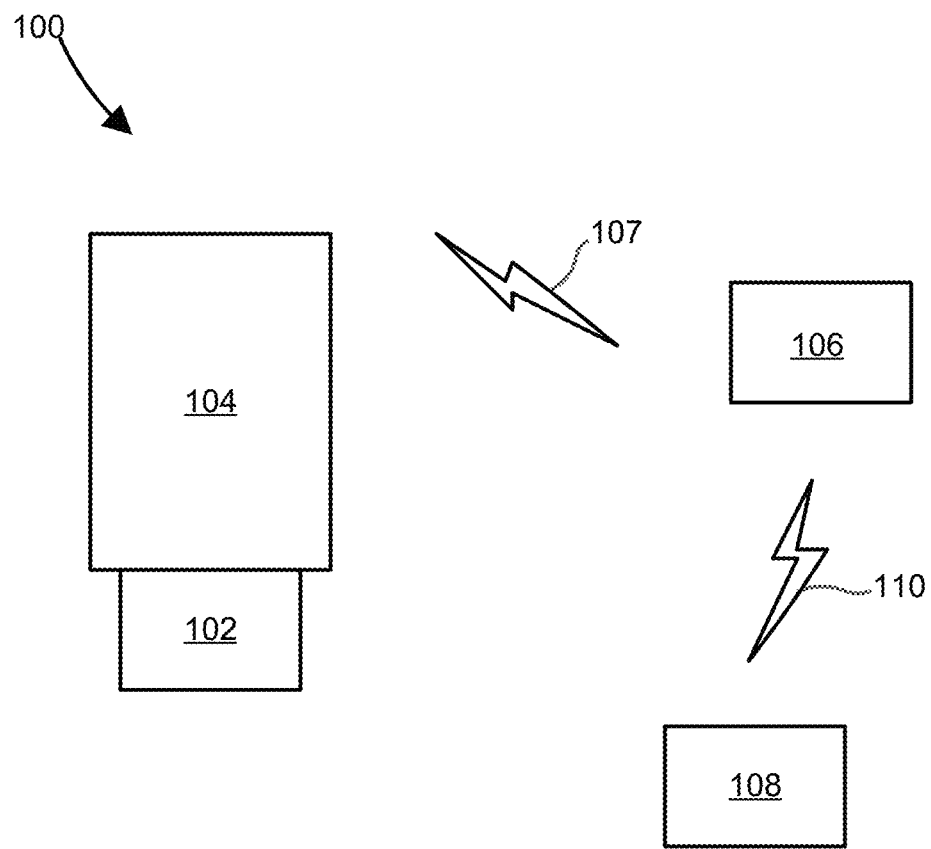
FIG. 1 is a schematic illustration of one embodiment of a skin cooling treatment system.

The present disclosure relates to systems, devices, and methods that improve the control of treatment. This improved control of treatment can be achieved by a system and/or by use of a system that includes a cryospray applicator coupled to a distal end of a mechanical arm that can be a multi-axis arm. The position and/or orientation of the cryospray applicator can be controlled by movement of the mechanical arm and/or by movement of one or several joints of the mechanical arm. The cryospray applicator can include one or several sensors that can detect, for example, a distance between the cryospray applicator and the skin being treated, the orientation of the cryospray applicator with respect to the skin being treated, and/or the cooling or temperature or color of the skin being treated. The mechanical arm can be controlled to sweep the cryospray applicator across the patient's skin to treat a desired area of skin The sweeping of the cryospray applicator can be controlled according to information received from one or several of the sensors including, for example, the temperature of the skin, the distance between the cryospray applicator and the skin being treated, and/or the orientation of the cryospray applicator with respect to the skin With reference now to FIG. 1, a schematic illustration of one embodiment of a skin cooling treatment system 100 is shown. The skin cooling treatment system 100 can include a cryospray applicator 102 that is coupled to a mechanical arm 104, and specifically to a distal end of the mechanical arm 104. The cryospray applicator 102 can be configured to deliver a coolant to a treated portion of skin In some embodiments, the cryospray applicator 102 can be configured to deliver a spray of cryogen towards and/or or onto a portion of skin being treated. This spray of cryogen can be delivered through one or several orifices, which orifices can comprise one or several nozzles. Embodiments of an exemplary cryospray applicator 102 including an array of orifices are disclosed in U.S. application Ser. No. 16/020,852, filed on Jun. 27, 2018, and entitled, "Dermatological Cryospray Devices Having Linear Array Of Nozzles And Methods Of Use", the entirety of which is hereby incorporated by reference herein. Further details of the mechanical arm 104 and the cryospray applicator 102 can be found in concurrently filed U.S. Provisional Application No. 62/784,124, filed on Dec. 21, 2018, and entitled "AUTOMATED DERMATOLOGICAL CRYOSPRAY TREATMENT PLANNING SYSTEM," the entirety of which is hereby incorporated by reference herein.

The mechanical arm 104 can have any desired number of axes of movement, and can, in some embodiments, be a 6-axis arm. In some embodiments, the mechanical arm 104 can have a single degree of freedom (e.g. a linear stage) which would allow control of movement along one axis, two degrees of freedom which would allow control of movement along two axes, three degrees of freedom, four degrees of freedom, five degrees of freedom, six degrees of freedom, and/or any other number of degrees of freedom. In some embodiments, the number of degrees of freedom can be selected based on the desired level of control and movement of the cryospray applicator. Thus, a higher number of degrees of freedom provide greater control of the position and/or orientation of the cryospray applicator 102. The mechanical arm 104 can be any of a number of currently commercially available mechanical arms. The mechanical arm 104 can be robotic and/or teleoperated.

The system 100 can include a controller 106 and/or processor 106 which can be communicatively coupled with the mechanical arm 104 and specifically with one or several actuators in the mechanical arm 104. In some embodiments, the communicating coupling of the controller 106 and the mechanical arm 104 can be via a wired or wireless connection, and the communicating coupling is indicated by lightning bolt 107. The processor 106 can comprise a microprocessor, such as a microprocessor from Intel® or Advanced Micro Devices, Inc.®, Ateml, Texas Instrument, or the like.

The controller 106 and/or processor 106 can generate control signals which can control the movement of the cryospray applicator 102. The control of the movement of the cryospray applicator 102 can allow the processor 106 to control: the sweeping of the cryospray applicator 102 across the patient's skin; the distance between the cryospray applicator 102 and the portion of skin being presently treated; and/or the orientation of the cryospray applicator 102 with respect to the portion of skin being presently treated.

The controller 106 can, in some embodiments, receive information relating to the desired area of skin for treatment and information relating to the treatment. With this information, the controller 106 can, in some embodiments, generate treatment paths, which treatment paths characterize the movement of the cryospray applicator 102 and the delivery of cooling the cryospray applicator 102. In some embodiments, the controller 106 can change these treatment paths during the providing of a treatment. In some embodiments, for example, the size of the portion of skin treated at any instant by the cryospray applicator 102 may vary based on, for example, the number of orifices in the array of orifices through which cryogen is sprayed, the distance between the portion of skin being treated and the cryospray applicator 102, or the like. In such embodiments, as the size of the portion of skin treated at any instant changes, the controller 106 can generate updated treatment paths to compensate for this change in the size of the portion of skin treated at any instant.

The controller 106 can be communicatingly connected with an user device 108. The user device can be distinct from the controller 106, or in some embodiments, the user device 108 can include the controller 106. The user device 108 can be any device configured to provide information to and receive inputs from a user, such as the user controlling the treatment provided by the skin cooling treatment system 100. The user device 108 can, in some embodiments, comprise a computing device such as a laptop, a tablet, a smartphone, a monitor, a display, a keyboard, a keypad, a mouse, or the like. In some embodiments, the communicating coupling of the controller 106 and the user device 108 can be via a wired or wireless connection, and the communicating coupling is indicated by lightning bolt 110.

Figure 2:
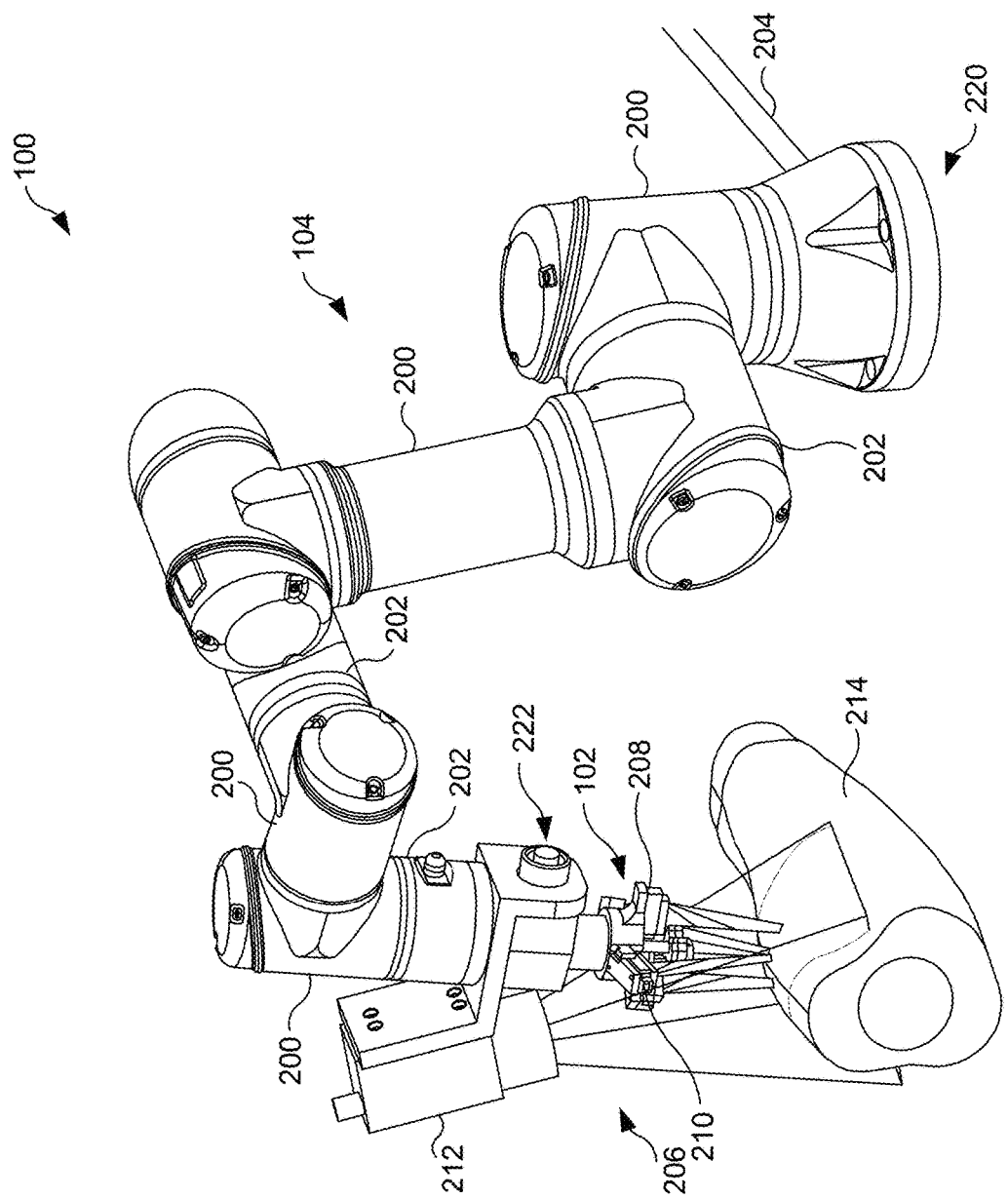
FIG. 2 is a perspective view of one embodiment of the skin cooling treatment system.

With reference now to FIG. 2, a perspective view of one embodiment of the skin cooling treatment system 100 is shown. The system includes the cryospray applicator 102 and the mechanical arm 104. As seen in FIG. 2, the mechanical arm 104 comprises a plurality of linkages 200 coupled by a plurality of joints 202, which joints 202 allow the relative movement of the linkages 200 with respect to each other. The mechanical arm 104 can further include a plurality of actuators, which actuators can, in response to control signals received from the controller 106, affect the relative position of some or all of the linkages 200 via movements of some or all of the joints 202 coupling linkages 200 to thereby affect the position and/or orientation of the cryospray applicator 102.

The mechanical arm 104 can further include one or several communication features such as cable 204. In some embodiments, the communication features, such as the cable 204 can communicatingly couple the mechanical arm 104, and specifically the actuators of the mechanical arm 104, to the controller 106.

The mechanical arm 104 further comprises a proximal end 220 and a distal end 222. In some embodiments, the proximal end 220 of the mechanical arm 104 can be secured to an object such as, for example, a floor, a table, a cart, a wagon, or the like. The distal end 222 of the mechanical arm 104 can be coupled to the cryospray applicator 102 and can move with respect to the proximal end 220 of the mechanical arm 104. In some embodiments, the processor 106 can be configured to control the distal end 222 of the mechanical arm 104 and/or to control the cryospray applicator 102.

The cryospray applicator 102 can include a plurality of sensors 206, which sensors can include one or several alignment sensors 208, one or several distance sensors 210, and/or one or several temperature detection features 212. These sensors 206 can, in some embodiments, sense information relating to the treatment of a patient 214, and specifically information relating to the treatment of some or all of the patient's skin In some embodiments, the sensors 206 can sense a distance between the cryospray applicator 102 and the patch of skin being presently treated and/or the alignment of the cryospray applicator 102 with respect to the patch of skin being presently treated. Although functions of the alignment sensors 208 and/or the distance sensors 210 are discussed below, it should be understood that these functions can be performed by the sensors 206 which can include one or both of the alignment sensors 208 and the distance sensors 210.

Figure 3:
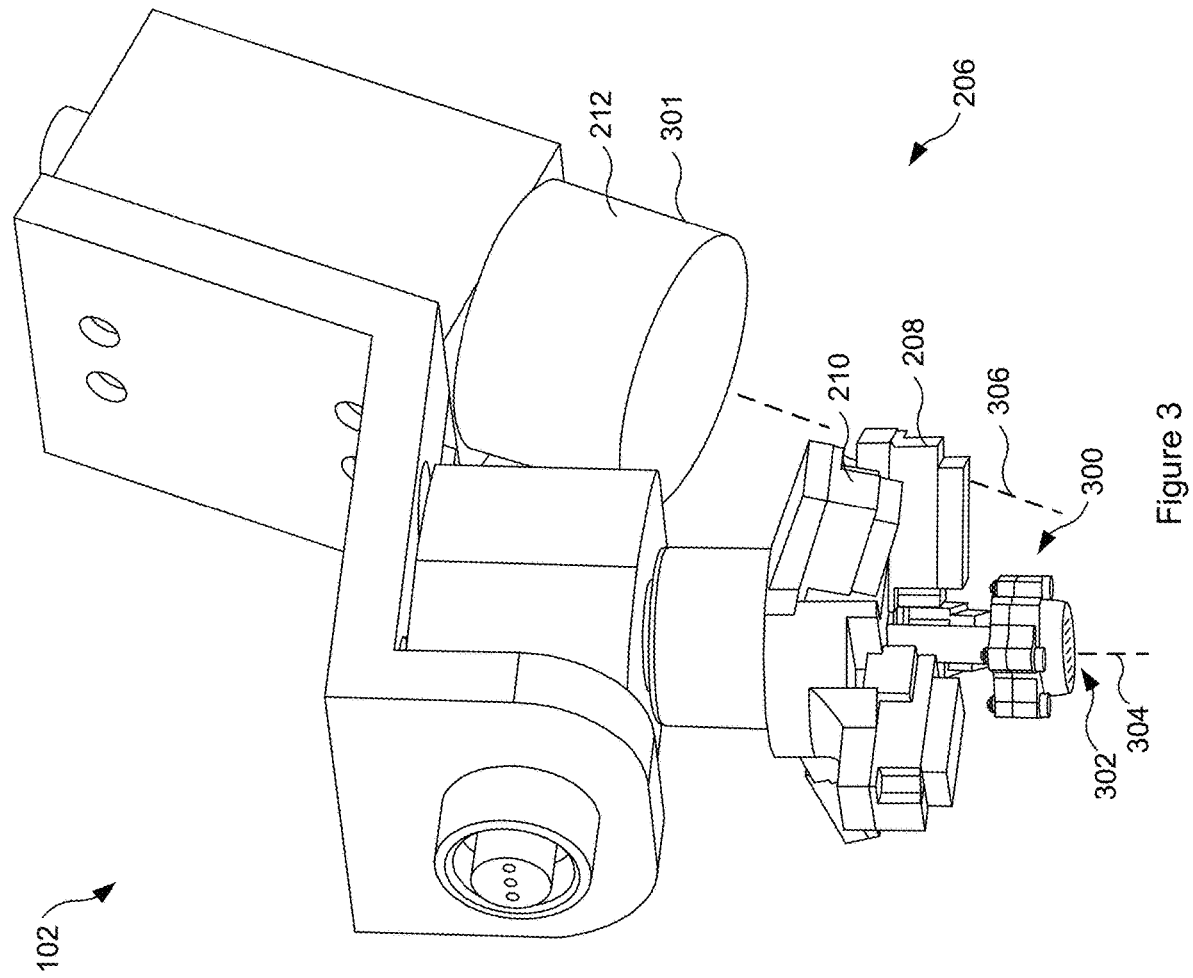
FIG. 3 is a perspective view of one embodiment of the cryospray applicator.

With reference now to FIG. 3, a perspective view of one embodiment of the cryospray applicator 102 is shown, which cryospray applicator 102 can be coupled to the distal end 222 of the mechanical arm 104. The cryospray applicator 102 includes a spray head 300 which comprises an array of orifices 302 through which cryogen can be sprayed towards and/or onto the patient's skin and specifically towards and/or onto a portion of the patient's skin being presently treated.

In some embodiments, the cryospray applicator 102 comprises the plurality of sensors 206, and specifically comprises one or more of: one or several alignment sensors 208; one or several distance sensors 210; or one or several temperature detection features 212. In some embodiments, the one or several temperature detection features 212 can be configured to: detect freezing of the portion of the patient's skin being presently treated; detect a temperature of the portion of the patient's skin being presently treated; detect a freezing rate of the portion of the patient's skin being presently treated, or the like. In some embodiments, the temperature detection feature can comprise a camera which can be a visible spectrum camera and/or an infrared camera 301, which infrared camera 301 can be pointed at the portion of the patient's skin being presently treated, or in other words, an axis 304, also referred to herein as "the line of spray 304", centrally extending through the array of orifices 302 intersects with an axis 306 central to the field of view of the infrared camera 301 such that the portion of skin being presently treated is within the field of view of the infrared camera 301.

Figure 4:
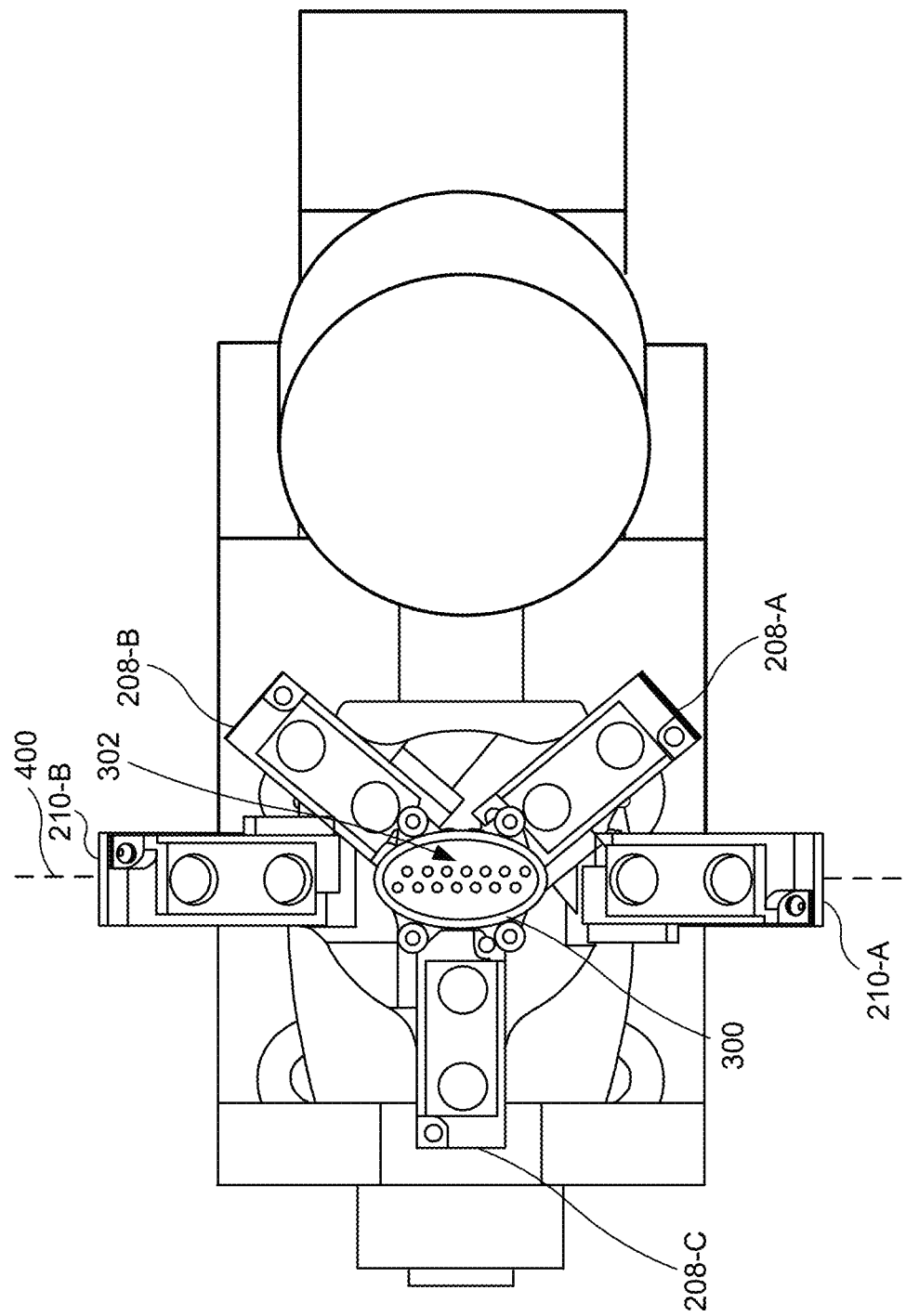
FIG. 4 is a bottom view of one embodiment of the cryospray applicator.

With reference now to FIG. 4, a bottom view of one embodiment of the cryospray applicator 102 is shown. As seen, the cryospray applicator 102 includes the spray head 300 and the array of orifices 302. In the embodiment of FIG.

4, the cryospray applicator 102 includes the one or several alignment sensors 208, which are configured to detect an orientation of the cryospray applicator 102, and specifically the orientation of the spray head 300 and/or the array of orifices 302, with respect to the portion of the patient's skin being presently treated. In some embodiments, the cryogen spray can cause deformation of the portion of the patient's skin tissue receiving a treatment, and the alignment sensors 208 can, in some embodiments, detect this deformation and/or can detect the orientation of the cryospray applicator 102 with respect to the deformed tissue.

Figure 5:
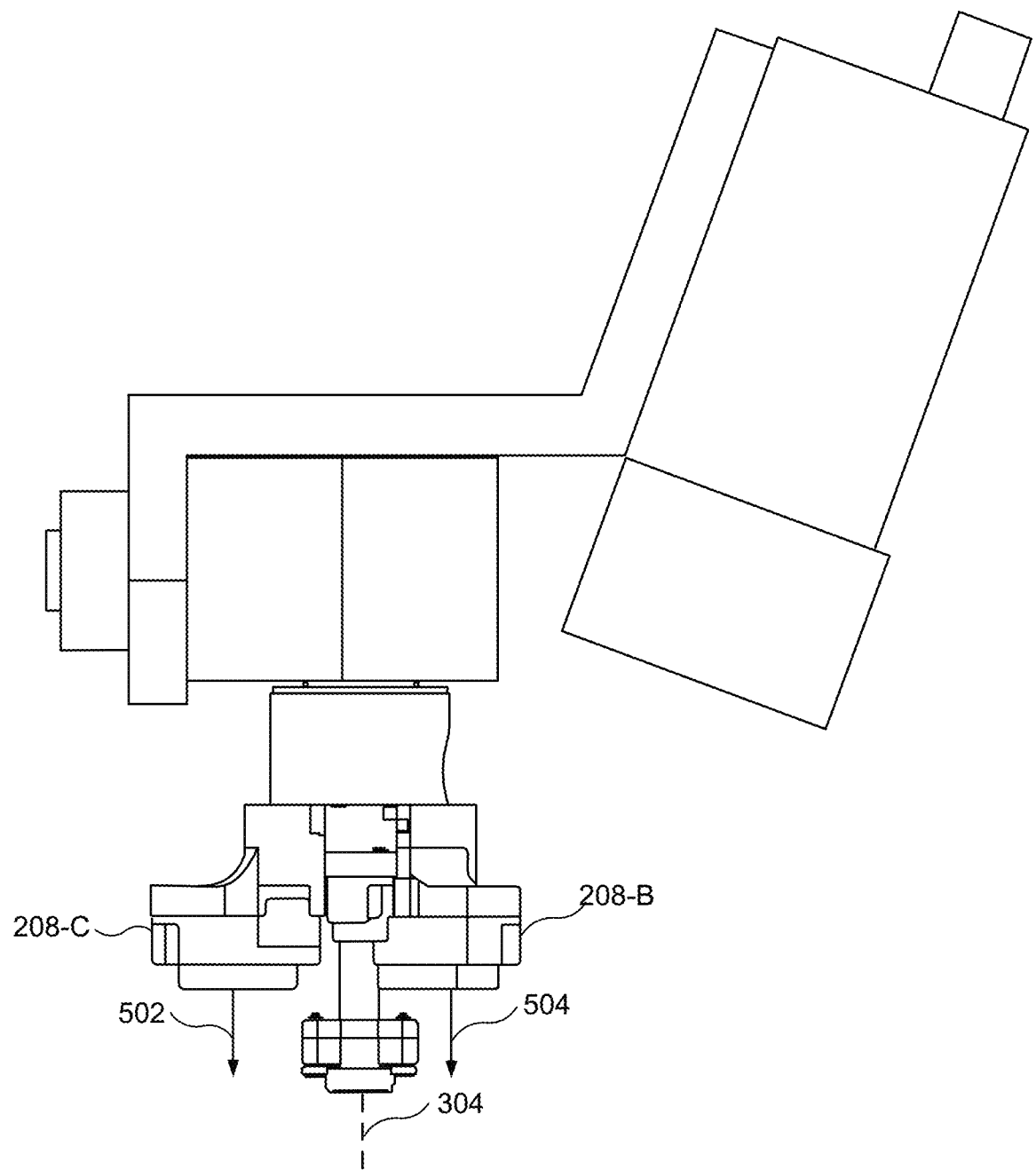
FIG. 5 is a side view of one embodiment of the cryospray applicator.

As seen in the embodiment of FIG. 4, the at least one alignment sensors 208 comprise three alignment sensors 208-A, 208-B, 208-C. These three alignment sensors 208-A, 208-B, 208-C are arranged around the spray head 300 and/or the array of orifices 302, and specifically are radially arranged around the spray head 300 and/or the array of orifices 302. In some embodiments, each of these three alignment sensors 208-A, 208-B, 208-C can face in a common direction. Specifically, and as shown in FIG. 5, a side view of one embodiment of the cryospray applicator 102, the three alignment sensors 208-A, 208-B, 208-C can each face in a common direction, specifically, each of a first alignment sensor 208-A, a second alignment sensor 208-B, and a third alignment sensor 208-C can face in a common direction (indicated by arrows 502, 504). In some embodiments, this common direction can be parallel to the direction in which the axis 304 centrally extending through the array of orifices 302.

The cryospray applicator 102 includes the one or several distance sensors 210 that can be configured to detect the distance from the cryospray applicator 102 and specifically from the spray head 300 and/or the array of orifices 302. In some embodiments, the one or several distance sensors 210 can comprise two distance sensors 210-A, 210-B. The distance sensors 210-A, 210-B can be arranged around the spray head 300 and/or around the array of orifices 302, and in some embodiments, radially arranged around the spray head 300 and/or around the array of orifices 302. In some embodiments, a first distance sensor 210-A is at a first position offset a first distance in a first direction from the array of orifices 302 and/or from the spray head 300, and the second distance sensor 210-B is at a second position offset a second distance in a second direction from the array of orifices 302 and/or from the spray head 300. In some embodiments, the first distance of offset of the first distance sensor 210-A can be equal to the second distance of offset of the second distance sensor 210-B. In some embodiments, the first distance sensor 210-A, the second distance sensor 210-B, and the spray head 300 and/or the array of orifices 302 can be linearly arranged such that, when viewed as shown in FIG. 4, a single axis 400 extends through each of the first distance sensor 210-A, the second distance sensor 210-B, and the spray head 300 and/or the array of orifices 302. In such an embodiment in which the first distance sensor 210-A, the second distance sensor 210-B, and the spray head 300 and/or the array of orifices 302 are linearly arranged, the first direction can be opposite to the second direction.

Figure 6:
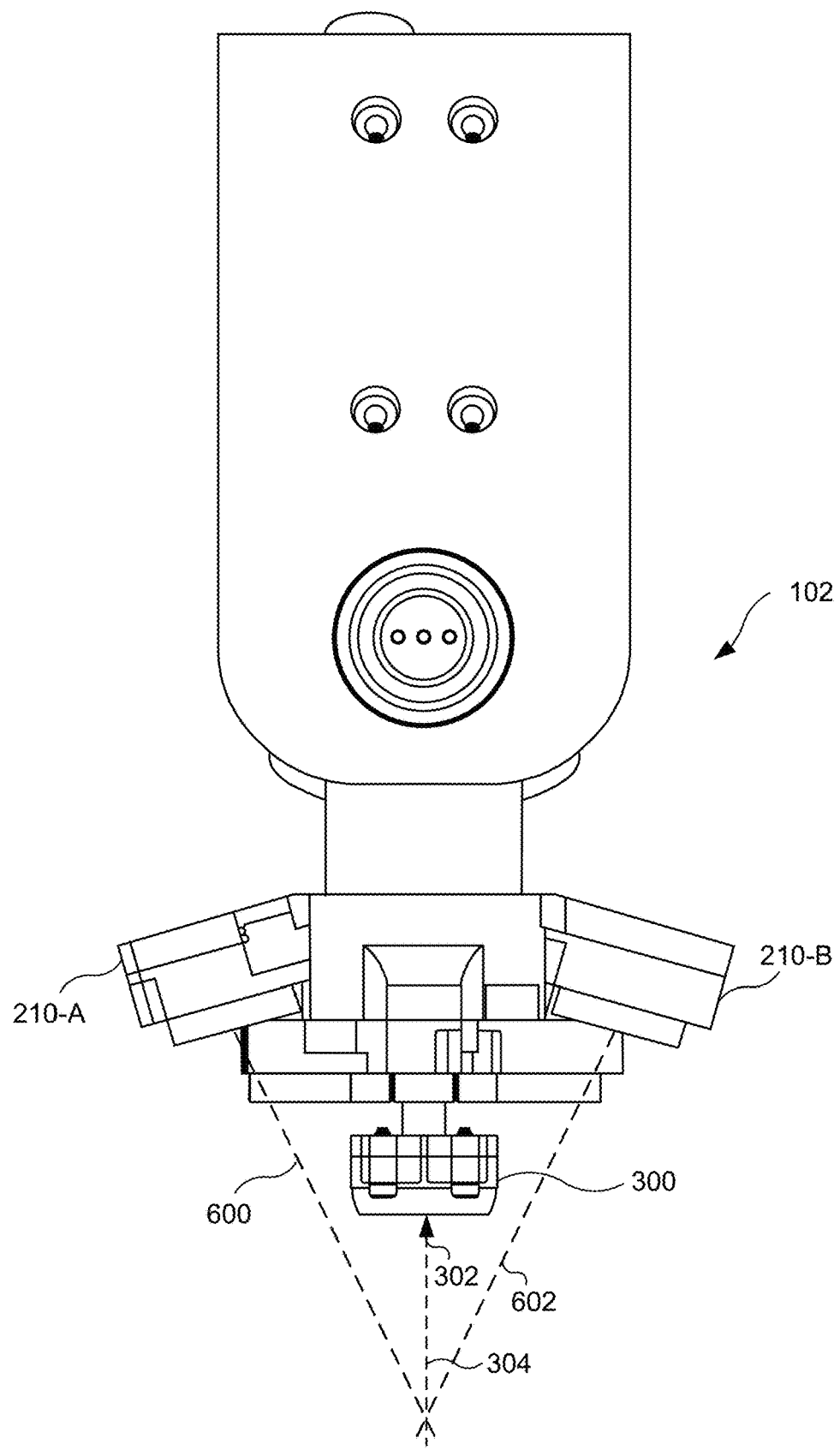
FIG. 6 is front view of one embodiment of the cryospray applicator.

As seen in FIG. 6, the cryospray applicator 102 includes the first distance sensor 210-A and the second distance sensor 210-B. The first distance sensor 210-A has a first orientation along a first distance axis 600, and the second distance sensor 210-B has a second orientation along a second distance axis 602. As seen, the first orientation of the first distance sensor 210-A is different from the second orientation of the second distance sensor 210-B. As further seen, the first orientation of the first distance sensor 210-A points the first distance sensor 210-A towards the line of spray 304 of the cryospray applicator 102 and the second orientation of the second distance sensor 210-B points the second distance sensor 210-B towards the line of spray 304 of the cryospray applicator 102. This pointing of the first distance sensor 210-A and of the second distance sensor 210-B towards the line of spray 304 is indicated by the intersection of each of the first and second distance axes 600, 602 and the line of spray 304. In some embodiments, this orientation towards the line of spray can facilitate measurement of the distance from the cryospray applicator 102 to the portion of skin being treated via the cryogen spray. In some embodiments, the cryogen spray can cause deformation of the portion of the patient's skin tissue receiving a treatment, and the orientation of the first and second distance sensors 210-A, 210-B towards the line of spray 304 can facilitate in including the effects of this deformation in the measure of distance between the cryospray applicator 102 and the portion of the patient's skin tissue receiving the treatment.

Figure 7:
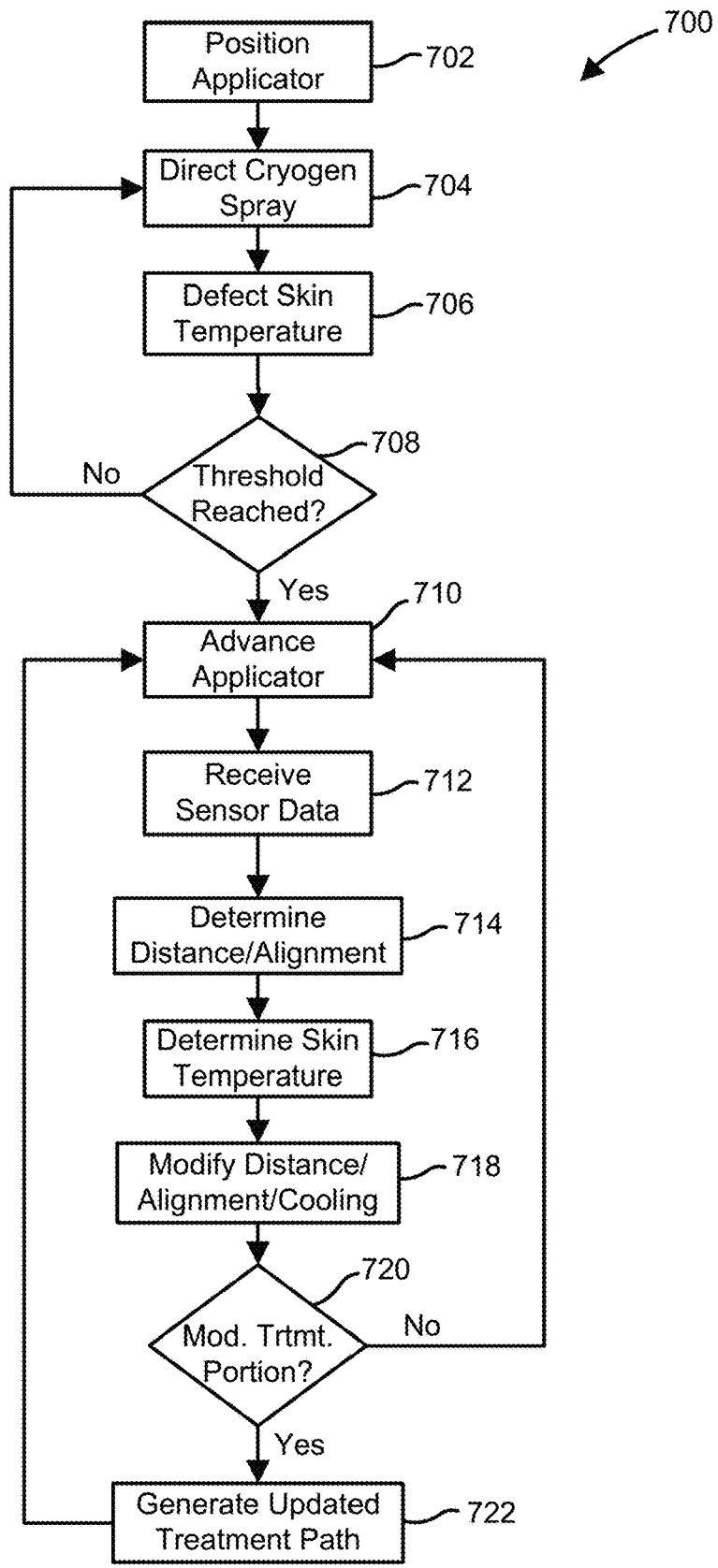
FIG. 7 is a flowchart illustrating one embodiment of a process for providing cooling treatment to skin tissue.

With reference now to FIG. 7, a flowchart illustrating one embodiment of a process 700 for providing a treatment to an area of skin of a patient is shown. The process can be performed using all or portions of the skin cooling treatment system 100, and specifically can be performed by the processor 106. In some embodiments, the process 700 can provide a method for cooling an area of skin of a patient as a part of a treatment.

The process 700 begins at block 702, wherein the cryospray applicator 102 is positioned proximate to a patient's skin tissue, and specifically, the cryospray applicator 102 is positioned proximate to an area of the patient's skin tissue, which area encompasses the patient's skin tissue to be treated. In some embodiments, the positioning of the cryospray applicator 102 proximate can be automatically performed via one or several movements of the mechanical arm 104 coupled to the cryospray applicator 102. As used herein, the "portion of the area" and/or the portion identifies the subset of skin tissue that is either presently being treated or that is positioned with respect to the cryospray applicator 102 so as to be treated, without movement of the cryospray applicator 102, by the dispensing of cryogen by the spray head 300. The positioning of the cryospray applicator 102 can further include: determining an initial distance separating the cryospray applicator 102 and the portion of the area of the patient's skin tissue; and adjusting the initial distance separating the cryospray applicator 102 and the portion of the area of the patient's skin tissue.

At block 704, cryogen is sprayed. In some embodiments, the cryogen can be sprayed through the array of orifices 302 in the spray head 300 of the cryospray applicator 102. This cryogen can be directed by the orifices in the array of orifices 302 to spray towards the portion of the area of the patient's skin tissue to be treated. The cryogen can be sprayed and/or directed to cool the portion of the area of skin tissue of the patient as a part of the treatment of the area of the patient's skin tissue and/or as a part of the treatment of the portion of the area of the patient's skin tissue. The cryogen can be sprayed by the opening of one or several valves fluidly coupled to the array of orifices 302 of the spray head 300 by one or several controls signals generated by the processor 102.

In some embodiments, the cryogen can be sprayed with sufficient force so as to deform the portion of the area of the patient's skin tissue. In some embodiments, for example, the spray of cryogen can impinge upon the portion of the area of the patient's skin tissue and can deform, and more specifically can depress, the portion of the area of the patient's skin tissue. The deformation can vary from patient to patient, and from treatment area to treatment area on a given patient, or even across a given treatment area, and can, for example, be based on the tautness of the patient's skin, the patient's body composition, or the like. In some embodiments, and to compensate for the deformation of the patient's skin, the directing of the cryogen spray can include a measuring of a distance between the cryospray applicator 102 and the portion of the area of the patient's skin tissue and adjusting this distance to be a desired value and/or to be within a desired range of distances.

At block 706, a skin temperature is detected. In some embodiments, the detected skin temperature can be the temperature of the portion of the area of skin tissue of the patient. This skin temperature can be detected by one or several temperature detection features 212 of the cryospray applicator 102, which features 212 can include, for example, an infrared camera. In some embodiments, the temperature sensed and/or measured can be a temperature of the portion of the area of skin tissue of the patient and/or can be an attribute relating to temperature. This attribute can include, for example: a cooling rate; or a freeze status—whether the portion of the area of skin receiving treatment. In some embodiments, for example, detecting the temperature of the portion of the area of skin tissue comprises: detecting freezing of the portion of the area of skin tissue; or detecting a cooling rate of the portion of the area of skin tissue of the patient. In some embodiments, the skin temperature can be detected by the features 212, and specifically by the infrared camera 301. Alternately color or change in color can be used to determine the freezing status of the skin. In some embodiments, this color and/or color change, and the determined freezing status can be used in making one or several treatment decisions.

After the temperature has been detected, the process 700 proceeds to decision state 708, wherein it is determined if a temperature threshold is reached. In some embodiments, this threshold can be retrieved from a memory associated with the processor 106. This threshold can vary based on one or more patient attributes, and/or based on the treatment being provided. In some embodiments, for example, the temperature threshold may be lower (e.g. identify a lower temperature) when some treatments are being performed, and in some embodiments, the temperature threshold may be higher (e.g. identify a higher temperature) when other treatments are being performed. In some embodiments in which skin lightening is being performed, the temperature threshold can be selected to achieve the desired decrease in pigmentation of the treated skin The detected skin temperature can be compared to the threshold. This comparison can be performed by the process 106. If it is determined that the threshold has not been reached, then the process 700 can return to block 704 and proceed as outlined above. If it is determined that the threshold has been reached, then the process 700 can proceed to block 710, wherein the cryospray applicator 102 is advanced. In some embodiments, the cryospray applicator 102 can be advanced by movement of all or portions of the mechanical arm, and specifically by the generation and sending of one or several control signals from the processor 106 to the mechanical arm, which control signals direct the movement of the mechanical arm 104 to advance the cryospray applicator 102. Thus, in some embodiments, the processor can be configured to control advancing of the cryospray applicator 102 via movement of the mechanical arm 104 to change the portion of skin being presently treated by the spray of cryogen. In some embodiments, the advance of the cryospray applicator 102 comprises the sweeping movement of the cryospray applicator 102 parallel to the surface of the patient's skin being treated. The advance of the cryospray applicator 102 can change the portion of the area of skin tissue of the patient being cooled by the cryogen spray and/or being treated.

At block 712, sensor data is received. In some embodiments, the sensor data can be received from some or all of the plurality of sensors 206, which sensors can include the one or several alignment sensors 208, the one or several distance sensors 210, and/or the one or several temperature detection features 212. The sensor data can be received by the processor 106. At block 714, the distance between the cryospray applicator 102 and/or the portion of the patient's skin being treated is determined and/or the alignment of the cryospray applicator 102 with respect to the portion of the patient's skin being treated is determined. The distance can, in some embodiments, be determined by the processor 106 based on data received from the one or several distance sensors 210 and/or, the alignment can, in some embodiments, be determined by the processor 106 based on data received from the one or several alignment sensors 208.

At block 716, the skin temperature and/or skin state is determined. In some embodiments, this skin temperature and/or skin state can be the measured temperature of the skin being treated, the color or change in color of the skin, a value indicative of the cooling and/or cooling rate of the skin being treated, a measure indicative of a freeze state, such as, for example, one or several values indicative of the start of freezing, of the skin being treated, one or several values indicative of a freezing rate of the skin being treated, or the like. In some embodiments, the skin temperature and/or skin state can be determined by the process 106 based on information received from the one or several temperature detection features 212, and specifically from the infrared camera.

At block 718, one or several of: the distance between the spray applicator 102 and the portion of skin being presently treated; the alignment of the spray applicator 102 with respect to the portion of skin being presently treated; and/or cooling applied by the spray applicator 102 to the portion of skin being presently treated is modified. In some embodiments, this modification is directed by controls signals generated by the processor 106, the control signals causing movement of all or portions of the mechanical arm 104. Thus, in some embodiments, the processor 106 can be configured to control: the distance between the cryospray applicator and the portion of skin being presently treated based on the outputs of at least one distance sensor 210; the alignment and/or orientation of the cryospray applicator with respect to the portion of skin being presently treated based on the outputs of at least one alignment sensor 208; and/or cooling of the portion of skin being presently treated. In some embodiments, the one or several of: the distance between the spray applicator 102 and the portion of skin being presently treated; the alignment of the spray applicator 102 with respect to the portion of skin being presently treated; and/or cooling applied by the spray applicator 102 to the portion of skin being presently treated, can be modified based on the determination of blocks 714 and 716.

In some embodiments, the modifying of the at least one of: the distance between the spray applicator 102 and the portion of skin being presently treated; the alignment and/or orientation of the spray applicator 102 with respect to the portion of skin being presently treated; and/or cooling applied by the spray applicator 102 to the portion of skin being presently treated, can comprise the automatic adjusting of the positioning of the cryospray applicator with respect to the portion of the skin tissue of the patient that is being presently treated. In some embodiments, this automatic adjusting of positioning can occur while the cryospray applicator is advancing.

In some embodiments, automatically adjusting the distance between the cryospray applicator 102 and the portion of skin being presently treated can include receiving sensor data from at least one of the sensors 206 and specifically from the at least one distance sensors 210, determining the distance between the cryospray applicator 102 and the portion of skin being treated based on the received sensor data, and generating control signals to control the mechanical arm 104 to achieve a desired distance between the cryospray applicator 102 and the portion of skin being treated. In some embodiments, the distance between the cryospray applicator 102 and the portion of skin being presently treated can be adjusted based, at least in part, on the deformation of the portion of skin being presently treated.

In some embodiments, automatically adjusting the alignment and/or orientation of the cryospray applicator 102 with respect to the portion of skin being presently treated can include, for example, receiving sensor data characterizing a detected orientation and/or alignment of the cryospray applicator 102 with respect to the portion of skin being presently treated from at least one of the sensors 206 and specifically from the at least one of the alignment sensors 208, determining with the processor 106 the alignment and/or orientation of the cryospray applicator 102 with respect to the portion of skin being presently treated, and generating control signals to control the mechanical arm 104 to achieve the desired alignment and/or orientation of the cryospray applicator 102 with respect to the portion of skin being treated. In some embodiments, the alignment and/or orientation of the cryospray applicator 102 with respect to the portion of skin being presently treated can be adjusted based, at least in part, on the deformation of the portion of skin being presently treated.

In some embodiments, modifying cooling of the portion of skin being presently treated can comprise at least one of: modifying advancing of the cryospray applicator 102; modifying the distance between the cryospray applicator 102 and the portion of skin being presently treated; and/or modifying a rate of cryogen delivery, e.g. the amount of cryogen sprayed on and/or towards the skin being presently treated in a period of time. In some embodiments, modifying of the distance between the cryospray applicator 102 and the portion of skin being presently treated can include: changing the distance between the cryospray applicator 102 and the portion of skin being presently treated by moving the cryospray applicator either closer to the portion of skin being presently treated or farther from the portion of skin being presently treated.

In some embodiments, modifying cooling can include the modifying of the advancing of the cryospray applicator 102. In some embodiments, for example, if decreased cooling is desired, the processor 106 can increase the rate of advance of the cryospray applicator 102 such that less cooling is applied to skin tissue as the cryospray applicator 102 advances past the skin tissue. In some embodiments, modifying cooling can include modifying the cryogen delivery rate. In some embodiments, the cryogen delivery rate can be modified by one or several valves that can decrease or increase the pressure of cryogen at the array of orifices 302. In some embodiments, the cryogen delivery rate can be modified by increasing or decreasing the number of open orifices in the array of orifices 302. In some embodiments, the number of orifices can be increased when increased cooling is desired and the number of orifices can be decreased when decreased cooling is desired.

After modifying of distance, alignment, and/or cooling, the process 700 proceeds to decision state 720, wherein it is determined if the size of the portion of skin being presently treated has changed. In some embodiments, the cryogen spray can expand as the spray travels away from the array of orifices 302 of the spray head 300. Thus, if the cryospray applicator 102 is moved closer to the portion of skin being presently treated, the cryogen spray will affect a smaller amount of tissue than before the move of the cryospray applicator 102, and similarly, if the cryospray applicator 102 is moved farther from the portion of skin being presently treated, the cryogen spray will affect a larger amount of tissue than before the move of the cryospray applicator 102. In some embodiments, the processor 106 can, based on the actions of step 718, determine if the size of the portion of skin being presently treated has changed. In some embodiments, this can include determining whether the distance between the cryospray applicator 102 and thus whether the size of the portion of skin being presently treated has changed. If it is determined that the size of the portion of skin being presently treated has not changed, and thus if it is determined that the distance between the cryospray applicator 102 and the portion of skin being presently treated has not changed, then the process 700 can return to block 710 and can proceed as outlined above.

If it is determined that that the size of the portion of skin being presently treated has changed, and thus if it is determined that the distance between the cryospray applicator 102 and the portion of skin being presently treated has changed, then the process 700 can proceed to block 722, wherein the processor 106 can update the treatment paths used in advancing the cryospray applicator 102 to compensate of this change in the size of the portion of skin being presently treated. In some embodiments, updating the treatment paths and/or generating updating treatment paths can include determining an updated size of the portion of skin being presently treated, and generating an updated treatment path based on the updated size of the portion of skin being presently treated. In some embodiments, the treatment path can identify the movements of the cryospray applicator 102 to provide the desired treatment. In embodiments in which the size of the portion of treated skin has decreased, updated treatment paths may be closer together than previously, and in embodiments in which the size of the portion of treated skin has increased, updated treatment paths may be further apart than previously. After the treatment paths have been updated, the process 700 returns to block 710 and proceeds as outlined above. In some embodiments, and at block 710, the cryospray applicator 102 is advanced according to the updated treatment paths.

The subject matter of the present invention is described here with specificity, but the claimed subject matter may be embodied in other ways, may include different elements or steps, and may be used in conjunction with other existing or future technologies.

This description should not be interpreted as implying any particular order or arrangement among or between various steps or elements except when the order of individual steps or arrangement of elements is explicitly described. Different arrangements of the components depicted in the drawings or described above, as well as components and steps not shown or described are possible. Similarly, some features and sub-combinations are useful and may be employed without reference to other features and sub-combinations. Embodiments of the invention have been described for illustrative and not restrictive purposes, and alternative embodiments will become apparent to readers of this patent. Accordingly, the present invention is not limited to the embodiments described above or depicted in the drawings, and various embodiments and modifications may be made without departing from the scope of the claims below.

What is claimed is:

1. A method of cooling an area of skin tissue of a patient, the method comprising:
    automatically positioning a cryospray applicator proximate to the area of skin tissue of the patient to be treated via movement of a mechanical arm coupled to the cryospray applicator;
    directing a continuous line of spray of cryogen through an array of orifices of the cryospray applicator to cool a portion of the area of skin tissue of the patient, wherein directing the continuous line of spray of cryogen through the array of orifices of the cryospray applicator to cool the portion of the area of skin tissue of the patient deforms the portion of the area of skin tissue of the patient;
    advancing the continuous line of spray by a sweeping movement via movement of the mechanical arm along the portion of the area of skin tissue of the patient cooled by the continuous line of spray of cryogen; and
    automatically adjusting positioning of the cryospray applicator with respect to the portion of the area of skin tissue of the patient while the cryospray applicator is advancing and while directing the continuous line of spray of cryogen through the array of orifices so that the portion of the area of skin tissue is continuously treated, and wherein at least one of: an orientation of the cryospray applicator is adjusted based at least in part on the deformation of the portion of the area of skin tissue of the patient, wherein the deformation comprises a depression; or a distance between the cryospray applicator and the portion of the area of skin tissue of the patient is adjusted based at least in part on the deformation of the portion of the area of skin tissue of the patient, wherein the deformation comprises a depression.

2. The method of claim 1, wherein automatically adjusting the distance between the cryospray applicator and the portion of the area of skin tissue of the patient comprises: detecting the distance between the cryospray applicator and the portion of the area of skin tissue of the patient with at least one distance sensor coupled to the cryospray applicator.

3. The method of claim 1, wherein automatically adjusting the orientation of the cryospray applicator with respect to the portion of the area of skin tissue of the patient comprises: detecting the orientation of the cryospray applicator with respect to the portion of the area of skin tissue of the patient with at least one alignment sensor.

4. The method of claim 1, further comprising: detecting a temperature of the portion of the area of skin tissue of the patient; and modifying at least one of: advancing the cryospray applicator; the distance between the cryospray applicator and the portion of the area of skin tissue of the patient; or a cryogen delivery rate, wherein detecting the temperature of the portion of the area of skin tissue of the patient comprises: detecting freezing of the portion of the area of skin tissue of the patient; or detecting a cooling rate of the portion of the area of skin tissue of the patient.

5. The method of claim 4, wherein modifying the distance between the cryospray applicator and the portion of the area of skin tissue of the patient comprises: changing the distance between the cryospray applicator and the portion of the area of skin tissue of the patient; determining an updated portion of the area of skin tissue of the patient based on the changed distance; generating an updated treatment path; and advancing the cryospray applicator according to the updated treatment path.

6. The method of claim 4, wherein modifying the cryogen delivery rate comprises at least one of: decreasing a number of open orifices in the cryospray applicator; or decreasing a cryogen pressure at the orifices in the cryospray applicator.

7. The method of claim 1, wherein the mechanical arm comprises at least one of: a 6-axis mechanical arm; or a robotic arm.

8. The method of claim 1, wherein positioning the cryospray applicator proximate to the area of skin tissue of the patient comprises moving the cryospray applicator over the portion of the area of skin tissue of the patient; determining an initial distance separating the cryospray applicator and the portion of the area of skin tissue of the patient; and adjusting the initial distance.

9. A skin cooling treatment system comprising:
    a mechanical arm having a proximal end and a distal end;
    a processor configured to control the mechanical arm; and
    a cryospray applicator coupled to the distal end of the mechanical arm, the cryospray applicator comprising an array of orifices, the cryospray applicator moveable in a sweeping manner by the mechanical arm to deliver a continuous line of spray of cryogen to a portion of an area of skin tissue of a patient for continuous treatment while moving the continuous line of spray, wherein the processor is configured to adjust at least one of: an orientation of the cryospray applicator based on a depression of the portion of the area of skin tissue from impingement of the cryogen on the portion of the area of skin tissue; or a distance between the cryospray applicator and the portion of the area of skin tissue of the patient based on a depression of the portion of the area of skin tissue from impingement of the cryogen on the portion of the area of skin tissue.

10. The system of claim 9, wherein the mechanical arm comprises at least one of: a 6-axis mechanical arm; or a robotic arm.

11. The system of claim 9, wherein the cryospray applicator comprises at least one distance sensor configured to detect the distance between the cryospray applicator and the portion of the area of skin tissue of the patient for treatment at which the continuous line of spray of cryogen is directed.

12. The system of claim 11, wherein the at least one distance sensor comprises two distance sensors arranged around the array of orifices, wherein the two distance sensors comprise: a first distance sensor at a first position offset from the array of orifices, the first distance sensor having a first orientation; and a second distance sensor at a second position offset from the array of orifices, the second distance sensor having a second orientation.

13. The system of claim 12, wherein the first orientation directs the first distance sensor towards the continuous line of spray of the cryospray applicator, and wherein the second orientation directs the second distance sensor towards the continuous line of spray of the cryospray applicator.

14. The system of claim 13, wherein the cryospray applicator comprises at least one alignment sensor configured to detect the orientation of the cryospray applicator with respect to the portion of the area of skin tissue of the patient.

15. The system of claim 14, wherein the at least one alignment sensor comprises three alignment sensors, each of the three alignment sensors facing in a common direction, the three alignment sensors radially arranged around the array of orifices of the cryospray applicator.

16. The system of claim 15, wherein the processor is configured to control movement of the distal end of the mechanical arm.

17. The system of claim 14, wherein the processor is configured to control the orientation of the cryospray applicator with respect to the portion of the area of skin tissue of the patient based on outputs of the at least one alignment sensor.

18. The system of claim 13, wherein the processor is configured to control movement of the cryospray applicator and the distance between the cryospray applicator and the portion of the area of skin tissue of the patient.

19. The system of claim 18, wherein the processor is configured to control the distance between the cryospray applicator and the portion of the area of skin tissue of the patient based on outputs of the at least one distance sensor.

20. The system of claim 9, wherein the cryospray applicator further comprises a temperature detection feature configured to detect a temperature of the portion of the area of skin tissue of the patient.

21. The system of claim 20, wherein the temperature detection feature is configured to detect at least one of: freezing of the portion of the area of skin tissue of the patient; or a cooling rate of the portion of the area of skin tissue of the patient.

22. The system of claim 21, wherein the processor is configured to: control advancing the cryospray applicator via movement of the mechanical arm to change the portion of the area of skin tissue of the patient cooled by the continuous line of spray of cryogen; detect a temperature of the portion of the area of skin tissue of the patient; and modify at least one of: the advancing the cryospray applicator; a distance between the cryospray applicator and the portion of the area of skin tissue of the patient; or a cryogen delivery rate.

23. The system of claim 22, wherein modifying the distance between the cryospray applicator and the portion of the area of skin tissue of the patient comprises: changing the distance between the cryospray applicator and the portion of the area of skin tissue of the patient; determining an updated portion of the area of skin tissue of the patient based on the changed distance; and generating an updated treatment path.

24. The system of claim 23, wherein the processor is configured to control advancing of the cryospray applicator according to the updated treatment path.

25. The system of claim 24, wherein modifying the cryogen delivery rate comprises at least one of: decreasing a number of open orifices in the cryospray applicator; or decreasing a cryogen pressure at the orifices in the cryospray applicator.

* * * * *